(12) United States Patent
Ross et al.

(10) Patent No.: US 11,638,623 B2
(45) Date of Patent: May 2, 2023

(54) RADIOGRAPHY AID FOR AN EXTERNAL FIXATOR

(71) Applicant: TEXAS SCOTTISH RITE HOSPITAL FOR CHILDREN, Dallas, TX (US)

(72) Inventors: John D. Ross, Ovilla, TX (US); Mikhail L. Samchukov, Coppell, TX (US); Alexander M Cherkashin, Flower Mound, TX (US)

(73) Assignee: Texas Scottish Rite Hospital for Children, Dallas, TX (US)

( * ) Notice: Subject to any disclaimer, the term of this patent is extended or adjusted under 35 U.S.C. 154(b) by 974 days.

(21) Appl. No.: 15/716,304

(22) Filed: Sep. 26, 2017

(65) Prior Publication Data

US 2018/0085183 A1    Mar. 29, 2018

Related U.S. Application Data

(60) Provisional application No. 62/399,769, filed on Sep. 26, 2016.

(51) Int. Cl.
*A61B 90/00* (2016.01)
*A61B 6/04* (2006.01)
(Continued)

(52) U.S. Cl.
CPC ............ *A61B 90/39* (2016.02); *A61B 5/4504* (2013.01); *A61B 6/04* (2013.01); *A61B 6/584* (2013.01);
(Continued)

(58) Field of Classification Search
CPC .......... A61B 90/39; A61B 6/04; A61B 6/584; A61B 17/3425; A61B 17/62; A61B 5/4504
See application file for complete search history.

(56) References Cited

U.S. PATENT DOCUMENTS 3,581,088 A * 5/1971 Engels ..................... A61B 6/04
                                                                    5/601
4,543,091 A * 9/1985 Froning ................. A61B 90/00
                                                                    604/116
(Continued)

OTHER PUBLICATIONS

International Search Report and Written Opinion dated Nov. 30, 2017 in connection with International Application No. PCT/US2017/053544, 10 pages.

*Primary Examiner* — David P Porta
*Assistant Examiner* — Meenakshi S Sahu
(74) *Attorney, Agent, or Firm* — Haynes and Boone, LLP

(57) ABSTRACT

A radiography aid and method of using the same comprising: attaching a radiographic reference device to the external fixation device, the radiographic reference device comprises at least two surfaces; positioning the first surface of the radiographic reference device on an imager surface to capture a first radiographic image of the external fixation device and the one or more objects; repositioning the external fixation device to position the second surface of the radiographic reference device on the imager surface to capture a second radiographic image of the external fixation device and the one or more objects that differs in position from the first radiographic image by the first angle; and calculating the position of the one or more objects in three dimensions.

32 Claims, 12 Drawing Sheets

(51) Int. Cl.
  *A61B 17/64*   (2006.01)
  *A61B 5/00*    (2006.01)
  *A61B 6/00*    (2006.01)
  *A61B 17/62*   (2006.01)
  *G03B 42/02*   (2021.01)

(52) U.S. Cl.
  CPC .......... *A61B 17/62* (2013.01); *A61B 17/6425* (2013.01); *A61B 2090/3966* (2016.02); *A61B 2090/3983* (2016.02); *G03B 42/02* (2013.01)

(56) References Cited

U.S. PATENT DOCUMENTS

| | | | |
|---|---|---|---|
| 5,485,856 A * | 1/1996 | Buckland | A61G 13/124 |
| | | | 128/879 |
| 6,701,174 B1 * | 3/2004 | Krause | G06T 17/10 |
| | | | 600/407 |
| 8,654,150 B2 | 2/2014 | Haskell | |
| 2004/0249375 A1 * | 12/2004 | Agee | A61B 17/6425 |
| | | | 606/54 |
| 2006/0017022 A1 | 1/2006 | Rigney et al. | |
| 2009/0003531 A1 * | 1/2009 | Fleig | A61B 6/04 |
| | | | 378/208 |
| 2010/0087819 A1 | 4/2010 | Mullaney | |
| 2010/0125273 A1 * | 5/2010 | Schwieger | A61B 17/683 |
| | | | 606/59 |
| 2013/0215114 A1 | 8/2013 | Cherkashin et al. | |
| 2016/0042571 A1 | 2/2016 | Mikheev et al. | |

\* cited by examiner

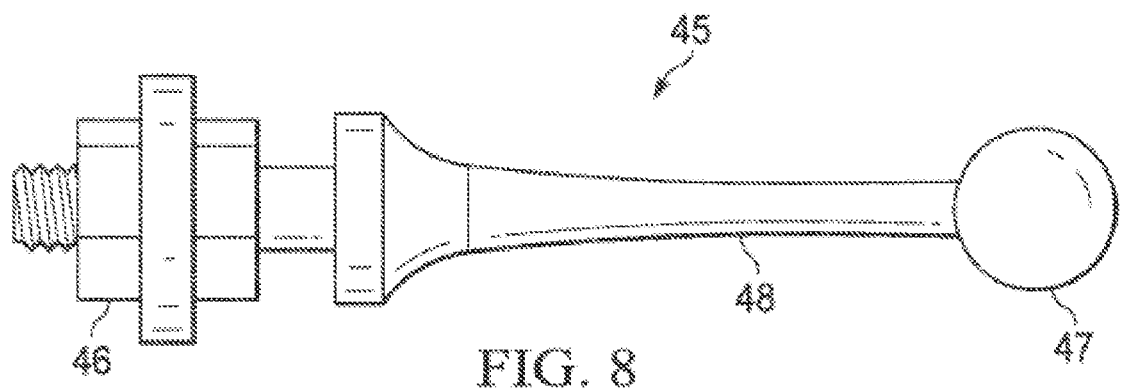

RADIOGRAPHY AID FOR AN EXTERNAL FIXATOR

CROSS-REFERENCE TO RELATED APPLICATIONS

This application claims the benefit of U.S. Provisional Application No. 62/399,769, filed at the U.S. Patent Office on Sep. 26, 2016, the entirety of which is hereby incorporated by reference into this application.

TECHNICAL FIELD

This disclosure relates in general to the field of radiography aids, and more particularly, to a radiography aid for an external fixator used for producing orthogonal radiographs.

BACKGROUND

Without limiting the scope of the invention, this background is provided in connection with radiographic aids. It is increasingly necessary to obtain three-dimensional (3D) digital images that faithfully reproduce the bone structure of a patient. Accurate 3D images can be used to more effectively plan, treat and assess the condition of a bone or bones. It is common to obtain digital images from radiographs that are carried out, to the best extent possible, in orthogonal planes. With the images obtained from the orthogonal radiographs of a particular bone of the patient, such as the tibia, it is possible to reconstruct the three-dimensional digital image of the bone. In order to achieve digitalization of a 3D form it is best if the radiographs are substantially perpendicular to each other, otherwise the currently available software may be unable to directly convert the data obtained from the radiographs.

The most commonly used radiographic equipment is suspended above a radiological table on which the patient lies so that part of his/her body or limb may undergo the radiography. To obtain radiographs that are perpendicular to each other, the patient must rotate his/her position or limb 90 degrees (90°) for the second radiograph to be generally perpendicular to the first radiograph. This operation of rotating through 90° the patient's body or limb becomes more difficult if the patient is fitted with an external fixator. In some circumstances, the equipment can be rotated 90°, but it is difficult to align the reference ring on both radiographic images and avoid overlapping of the bone image with the ring image.

Various systems and techniques are known for using orthogonal radiographs to recreate a three-dimensional models of a patient's body. One technique is described in U.S. Patent Application Publication No. 2016/0042571, the contents of which are hereby incorporated by reference into this application.

SUMMARY

In one embodiment, this disclosure relates to a method of determining the position of one or more objects affixed to an external fixation device in three dimensions comprising: attaching a radiographic reference device to the external fixation device, wherein the radiographic reference device comprises at least two surfaces separated by a first angle, wherein the at least two surfaces of the radiographic reference device are positioned at a second angle relative to a longitudinal axis of the external fixation device; positioning the first surface of the radiographic reference device on a surface to capture a first radiographic image of the external fixation device and the one or more objects; repositioning the external fixation device to position the second surface of the radiographic reference device on the surface to capture a second radiographic image of the external fixation device and the one or more objects that differs in position from the first radiographic image by the first angle; and calculating the position of the one or more objects in three dimensions based on distances measured from the first and second radiographic images with the first and second angles. In one aspect, the radiographic reference device is attached to the external fixation device with one or more rods or struts. In another aspect, the first and second angles are selected from 30°, 45°, 60°, 75°, 90°, 105°, 120°, or 150° degrees. In another aspect, the method further comprises positioning a size marker attached to at least one of the external fixation device, the strut or the radiographic reference device, wherein the size marker provides a known size to calibrate the distances measured in the first and second radiographic images. In another aspect, the one or more struts are adjustable struts. In another aspect, the radiographic reference device is at least partially radiotranslucent. In another aspect, the radiographic reference device is plastic, polymer, metal, ceramic, wood, or a composite. In another aspect, the radiographic reference device is defined further as comprising a slot adapted to receive the one or more struts. In another aspect, the radiographic reference device is substantially flat. In another aspect, the radiographic reference device further comprises one or more storage compartments for storing one or more radiographic markers and the one or more struts. In another aspect, the one or more objects comprise at least one bone. In another aspect, the first and second surfaces of the radiographic reference device are defined further as comprising a first and second arm, respectively. In another aspect, each of the first and second arms comprise longitudinal slits that extend longitudinally along the respective arm and are substantially perpendicular to each other. In another aspect, the method further comprises attaching a radiographic marker to the radiographic reference device and/or the external fixation device. In another aspect, the radiographic reference device has a right-angled shape with the first and second arms having substantially the same length.

In another embodiment, this disclosure relates to a system for determining the position of one or more objects affixed to an external fixation device in three dimensions comprising: a radiographic reference device attachable to the external fixation, wherein the radiographic reference device comprises at least two surfaces separated by a first angle, wherein the at least two surfaces of the radiographic reference device are positioned at a second angle relative to a longitudinal axis of the external fixation device; a first and a second radiographic image taken with a radiography device, wherein the first radiographic image is acquired when the first surface of the radiographic reference device is on a surface, and the second radiographic image is taken when the second arm of the radiographic reference device is on the surface; and a processor that calculates the position of the one or more objects in three dimensions based on distances measured from the first and second radiographic images with the first and second angles. In one aspect, the system further comprises one or more rods or struts, wherein the radiographic reference device is attached to the external fixation device with the one or more struts. In another aspect, the first and second angles are selected from 30°, 45°, 60°, 75°, 90°, 105°, 120°, or 150° degrees. In another aspect, the system further comprises a size marker attached to at least one of the external fixation device, the strut or the radiographic reference device, wherein the size marker provides a known size to calibrate the distances measured of the first and second radiographic images. In another aspect, the one or more struts are adjustable struts. In another aspect, the radiographic reference device is at least partially radiotranslucent. In another aspect, the radiographic reference device is plastic, polymer, metal, ceramic, wood, or a composite. In another aspect, the radiographic reference device is defined further as comprising a slot adapted to receive the one or more struts. In another aspect, the radiographic reference device is substantially flat. In another aspect, the radiographic reference device further comprises one or more storage compartments for storing one or more radiographic markers and the one or more struts. In another aspect, the one or more objects comprise at least one bone. In another aspect, the first and second surfaces of the radiographic reference device are defined further as comprising a first and second arm, respectively. In another aspect, each of the first and second arms comprise longitudinal slits extend longitudinally along the respective arm and are substantially perpendicular to each other. In another aspect, the radiographic reference device has a right-angled shape with the first and second arms having substantially the same length. In another aspect, the system further comprises a radiographic marker adapted to be attached to the radiographic reference device and/or the external fixation device.

In another embodiment, this disclosure relates to a method of taking substantially orthogonal radiographs comprising: attaching a radiographic reference device to an external fixation device, which external fixation device is adapted for attachment to one or more bones, wherein the radiographic reference device comprises at least a first arm and a second arm separated by a 90 degree angle, wherein the first arm and the second arm of the radiographic reference device are positioned perpendicular to a longitudinal axis of the external fixation device; positioning the first arm of the orthogonal radiographic reference device on a surface to capture a first radiographic image of the external fixation device; and repositioning the external fixation device and the radiographic reference device to position the second arm of the radiographic reference device to capture a second radiographic image of the external fixation device that is orthogonal to the first radiographic image.

In yet another embodiment, this disclosure relates to a radiography aid for an external fixator, characterized in that the radiographic aid comprises: a first and a second arm along a plane, wherein the first and a second arms are separated by a 90 degree angle; at least one opening for attachment to an external fixator when the external fixator is adapted to be mounted and fixed onto a bone; and at least one size marker attached to the radiography aid, the external fixator, or the strut.

BRIEF DESCRIPTION OF THE DRAWINGS

For a more complete understanding of the features and advantages of the present disclosure, reference is now made to the detailed description, along with the accompanying figures and in which:

FIG. 8 shows an alternative embodiment for a centering pin that can be used to measure distances and positions of fixator devices in radiographs;

DETAILED DESCRIPTION

While the making and using of various embodiments of the present disclosure are discussed in detail below, it should be appreciated that the present disclosure provides many applicable inventive concepts that can be embodied in a wide variety of specific contexts. The specific embodiments discussed herein are merely illustrative of specific ways to make and use the invention and do not delimit its scope.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

This disclosure relates to a radiography aid for use with an external fixator that is able to avoid the drawbacks mentioned above (lack of perpendicularity, ease of use, patient convenience), so that radiographs are truly perpendicular to each other, while ensuring flexibility of use also in the case of patients fitted with external fixators.

Another benefit of the disclosed technique is to ensure easy manoeuvrability for operators in the sector when adjusting and calibrating the radiography equipment so that it may be readily applied by unskilled or untrained operators, all of which within the context of a simple and rational constructional solution.

As used herein, the terms "radiolucent," "radiotranslucent," or "radiolucent material" refer to a material that is entirely transparent to radiation and/or almost entirely transparent in x-ray images and/or almost entirely transparent under fluoroscopy and/or other imaging modalities. Non-limiting example of radiolucent materials include a polymer, for example, but not limited to: polypropylene, polyethylene, polyether ether ketone, polyaryletherketone, acrylonitrile butadiene styrene, or nylon. Other non-limiting examples of materials include plastic, para-aramid synthetic fiber, resins (e.g., polyether imide), carbon fiber or carbon composite, wood, or cellulose.

Figure 1A:
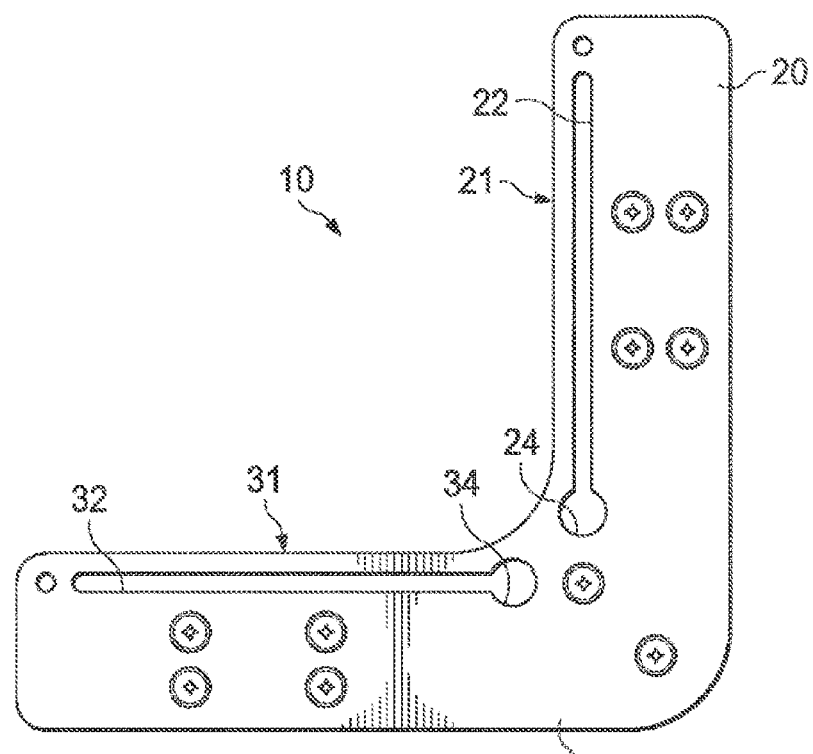
FIG. 1A depicts a front view of a radiography aid according to this disclosure.
Figure 1B:
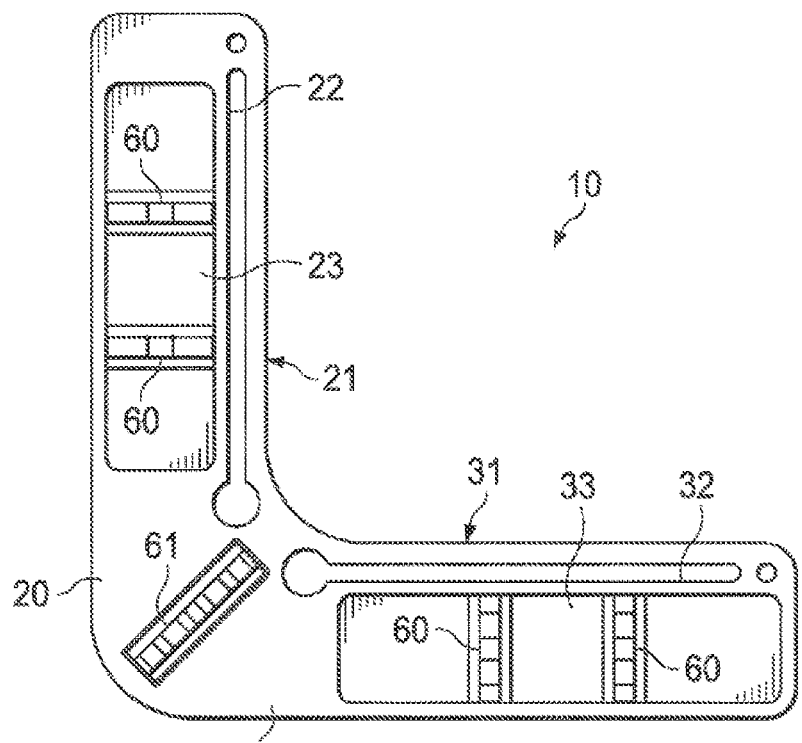
FIG. 1B depicts a rear view of a radiography aid according to this disclosure.
Figure 1C:
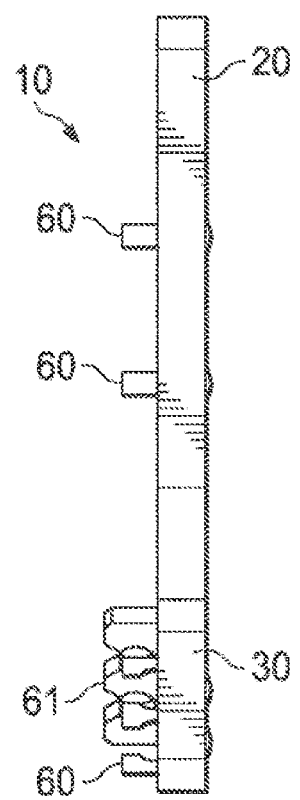
FIG. 1C depicts a side view of a radiography aid according to this disclosure.

Three different views of one embodiment of a radiography aid are depicted in FIG. 1A-1C. The radiography aid comprises a radiographic body 10 made of material which is, e.g., partially radiolucent. This radiographic body 10 comprises a first arm 20 having a first wall 21 and a second arm 30 having a second wall 31 arranged with precision at right angles to the first wall 21. Each of these arms 20, 30 of the radiographic body 10 may be furthermore provided with longitudinal slits 22, 32 parallel to the respective walls 21, 31 and terminating in apertures 24, 34 of sufficient size to permit the insertion and connection of fasteners, rods, or struts, which are able to ensure connection of the body 10 to an external fixator (shown in FIG. 3) when the fixator is mounted and fixed onto a patient's bone. According to one embodiment, once the fasteners or struts are passed through apertures 24, 34, they may slide along the length of longitudinal slits 22, 32 so that the body 10 can be placed in a preferable arrangement with respect to the fixator and/or the patient's body or limb.

The radiographic body 10 may be comprised of a unitary piece, for example produced by extrusion moulding, if synthetic polymer plastic material is used, it can be sintered, compressed, or even milled from a solid piece of the material using a controlled numerical control (CNC) machine.

According to one embodiment, the radiographic body 10 has an "L" or substantially right-angled shape with the respective arms having the same length and extending at 90° relative to each other. A placement of the arms at 90° relative to each other is preferable. In other embodiments, not depicted, the radiographic body 10 will have the at least two surfaces at 90 degree angles, but can be a triangle, a cube, a rectangle or other shapes so long as at least two surfaces are at 90 degree angles. In the example shown, the arms 20, 30 can be connected together by a curved connecting section, with the interior and exterior surfaces having a curvature, but the arms 20, 30 can also be connected with straight lines at one or more angles, e.g., a 45 degree angle) or even a 90 degree angle between the two surfaces. In the example shown, the arms 20, 30 are identical to each other and have a substantially parallelepiped configuration, with the respective longitudinal edges positioned perpendicular so as to form the two walls 21, 31 perpendicular to each other. The longitudinal slits 22, 32 extend longitudinally along the respective arms 20, 30 and are also perpendicular to each other.

Figure 2:
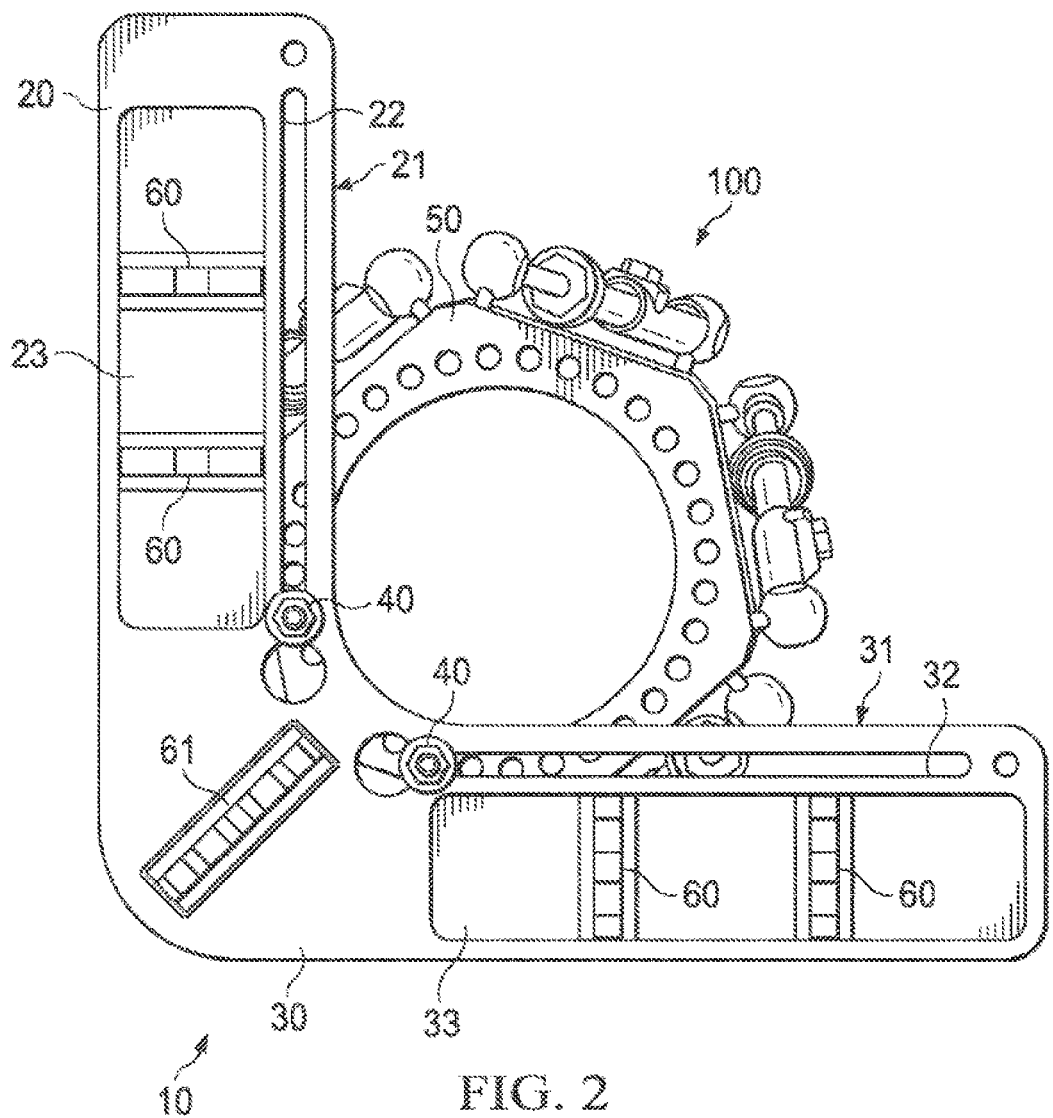
FIG. 2 shows a view of the radiography aid according to FIGS. 1A-1C that is slidably connected directly to an external fixator ring.
Figure 3:
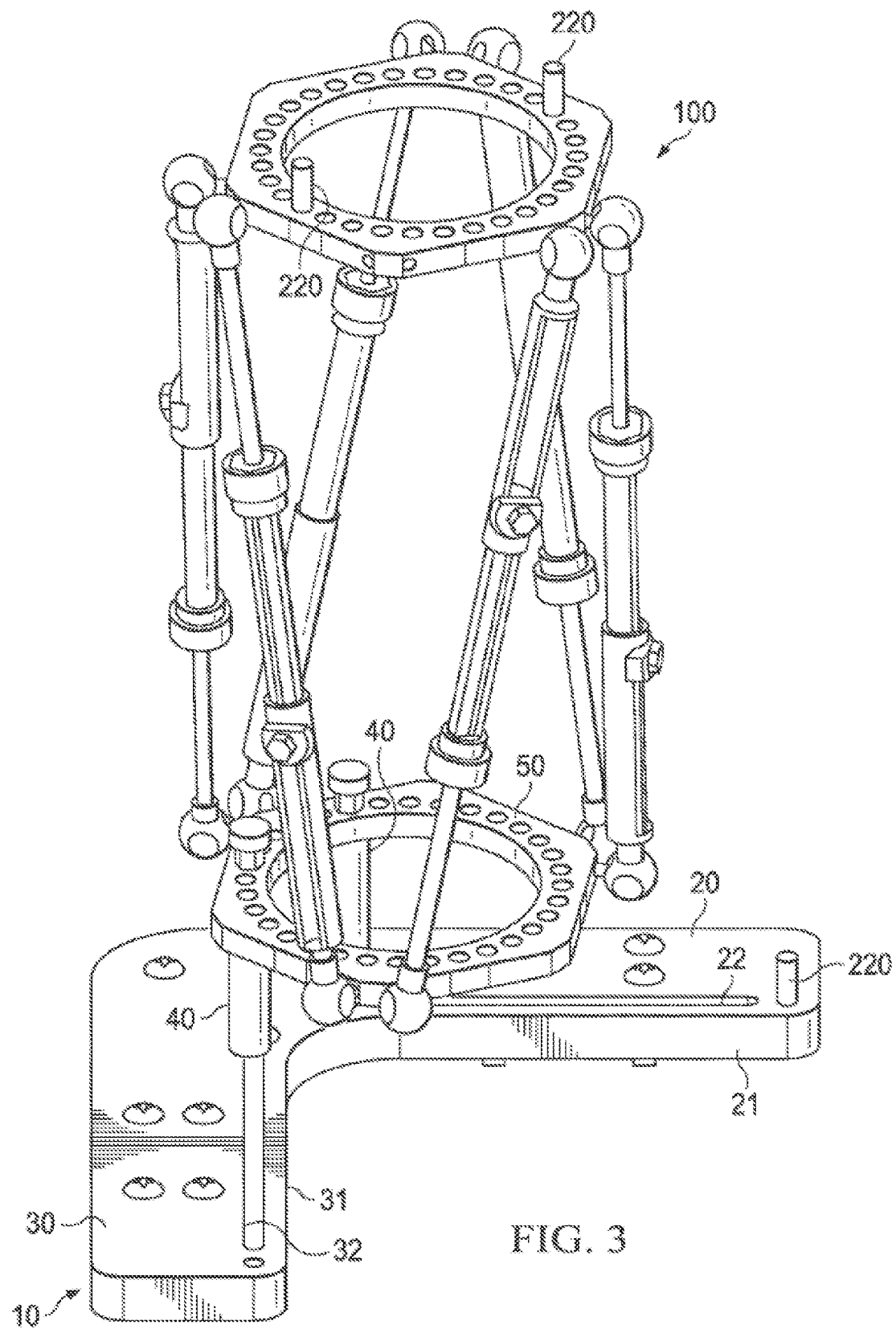
FIG. 3 shows a perspective view of the radiography aid according to FIGS. 1A-1C that is slidably connected to an external fixator ring via struts.

The width of the apertures 24, 34 will generally be selected to allow the insertion of a fastener such as a bolt (not depicted) or a rod, or strut 40, such that the radiographic body 10 can be affixed to an external fixation device, in the example shown in FIGS. 2 and 3, an external bone fixation device 100 is shown. While a six-sided external fixation device is depicted, external bone fixation device of any shape can be used. The rod or strut 40 may comprise a spacer stem with threaded opposite ends.

As shown in FIGS. 2 and 3, the rod or strut 40 can be fixed via one of its ends to the radiographic body 10 passing through the apertures 24, 34 and sliding into an appropriate location along in the slots 22, 32 and via the other opposite end fixed to an external fixation ring 50. The lengths of the longitudinal slits 22, 32 with apertures 24, 34 at their ends is such as to allow insertion of the end of the rod with the bolt already mounted through the apertures 24, 34 and sliding and positioning of the rod 40 at the most suitable point, followed by tightening of the bolt depending on the diameter of the ring of the an external bone fixation device 100. Once the external fixation ring 50 is fixed to the radiographic body 10 via rods or struts 40, the external fixation ring 50 and the radiographic body 10 are rigidly fixed together. Therefore, rotation of the external fixation ring 50 also causes rotation of the radiographic body 10 and vice versa.

This joining arrangement allows positioning of the external bone fixation device 100, the external fixation ring 50 of which is fixed to the radiographic body forms an integral part thereof, in the two positions which are at right angles to each other and which can be obtained by means of the radiographic body 10 having the arms 20, 30 with the walls 21, 31 perpendicular to each other. In other words, since the patient's bone is rigidly connected to the external bone fixation device, the patient's bone(s) will also be rigidly connected to the radiographic body when the latter is fastened to the external bone fixation device. An external fixation system suitable for use with the disclosed radiographic body 10 is the TRUELOK® and TL-HEX Ring Fixation Systems developed by Texas Scottish Rite Hospital for Children and sold by Orthofix, Inc.

As shown in FIG. 3, according to one embodiment of this disclosure, the radiographic body 10 can include an imprint for the insertion of one or more snap-engaging elements suitable for accessories for use with the radiographic body 10. The accessories can include, e.g., bolts, fasteners or struts to connect the radiographic body 10 the external bone fixation device, or even provide one or more radiographic markers that can be attached to the radiographic body 10 and/or the external bone fixation device 100 that provide a known size and/or shape in the radiographs to calibrate the distances measured in the first and second radiographic images. As shown in FIG. 3, a set of radiographic markers 220 are depicted as being attached to one of the rings and to the arm 20. These markers, when used with the known dimensions of the rings and the device 10, can help determine the three-dimensional position of the imaged portion of the body on the radiograph, through known techniques. The radiographic body 10 may be adapted to carry bolts, fasteners, and/or rods or struts 40 with the associated end fasteners (e.g., bolts) such that the user has a single device that includes the various attachments and markers. In certain other embodiments, one or more levelling instrument, such as, e.g., a tubular spirit, bull's eye, or water level, can be positioned in the radiographic body 10 to provide information about the position of the radiographic body 10 with regard to the ground at one or more positions.

In the example shown, each arm 20, 30 can be provided with a respective recess 23, 33 on which a pair of snap-engaging seats 60 made of resilient material can be included to provide storage for fixators, bolts, nuts, rods, shafts, markers, radiographic markers, or even one or more levels. Such is not a requirement for this invention though. It is also possible to provide a further recess or opening with smaller dimensions in the corner portion between the arms 20, 30 to insert a further snap-engaging seat 61 or opening for a fastener, rod or shaft. These snap-engaging seats can be used to releasably connect fasteners, rods, struts, or other devices to attach the radiographic body 10 to the external bone fixation device 100.

Figure 4:
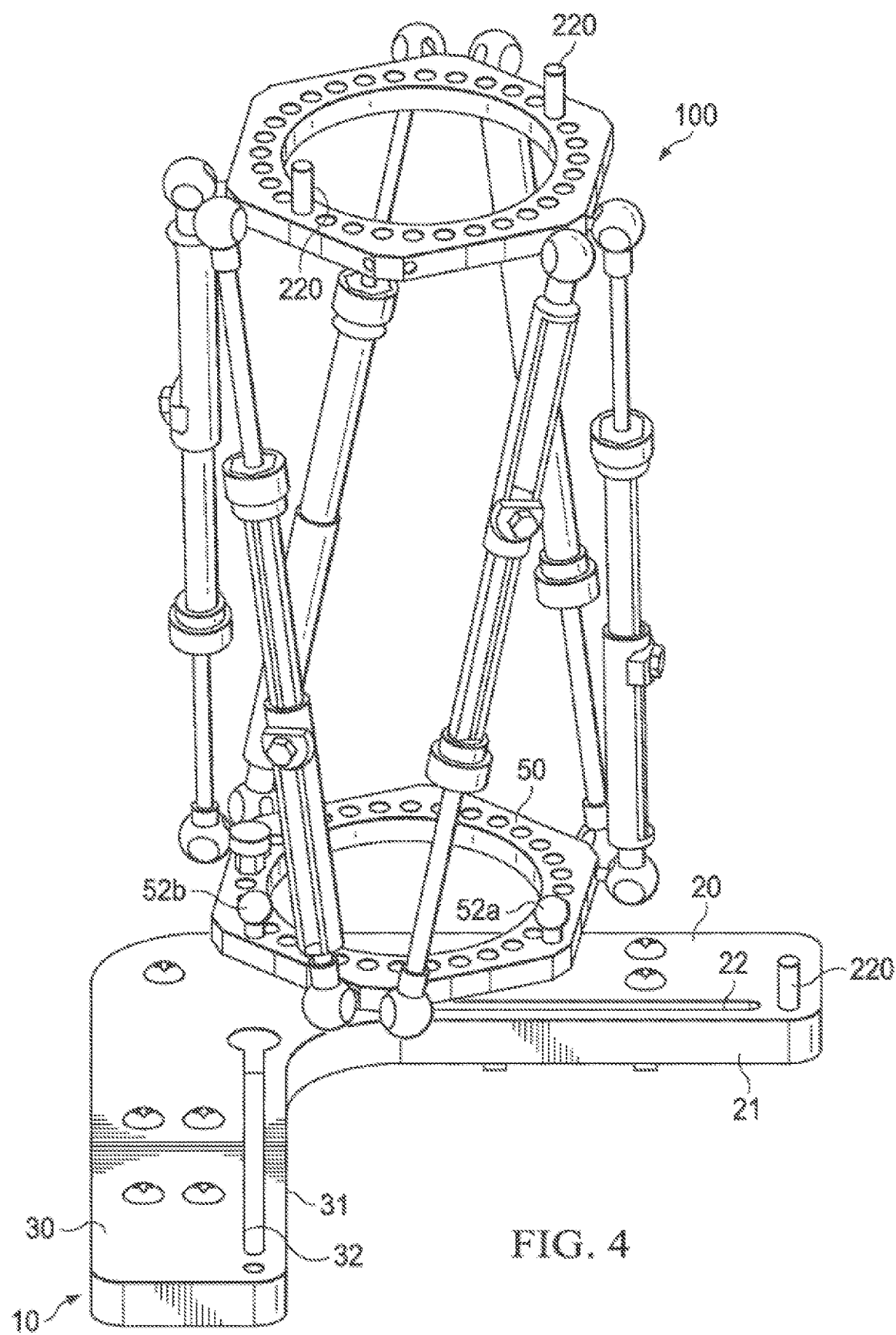
FIG. 4 shows a perspective view of the radiography aid according to FIGS. 1A-1C that is directly connected to an external fixator ring.

In FIG. 4, the radiographic body 10 is directly bolted to the ring 50 of the external bone fixation device 100 via bolts 52a and 52b. The accessories can include, e.g., bolts, fasteners or struts to connect the radiographic body 10 to the external bone fixation device, or even provide one or more radiographic markers that can be attached to the radiographic body 10 and/or the external bone fixation device 100 that provide a known size and/or shape in the radiographs.

The radiography aid according to the present disclosure is fixed using one or more bolts, rods or struts 40, which are affixed or locked at one of their ends together with the outermost ring 50 of the external bone fixation device 100 and at the other ends are fixed to each arm 20, 30, passing through the longitudinal slits 22, 32 with apertures, or apertures on the radiographic body 10. The apertures are depicted on the surface of the arms 20, 30 (which can be threaded apertures), however, apertures may also be provided, e.g., threaded apertures, along the surfaces of the side walls 21, 31 or even the side walls of the ends of the arms 20, 30, or on the surfaces opposite side walls 21, 31. Thus, the radiographic body 10 can also be attached by its ends or the opposite side of the walls 21, 31, so long as the device provides a way to take radiographs or other images at 90 degree angles. To provide more stable attachment, it may be common to attach the radiographic body 10 to the external bone fixation device 100 with two or more bolts, rods or struts 40. Suitable nuts and bolts, wing-nuts, lock-nuts, fasteners, or suitable end bolts used to lock the rods or struts 40, can be used to attach the radiographic body 10 to the external bone fixation device 100. Also shown in FIG. 4 is a set of radiographic markers 220 that are attached to one of the rings and to the arm 20. These markers, when used with the known dimensions of the rings and the device 10, can be used to help determine the three-dimensional position of the imaged portion of the body on the radiograph, through known techniques.

Figure 5:
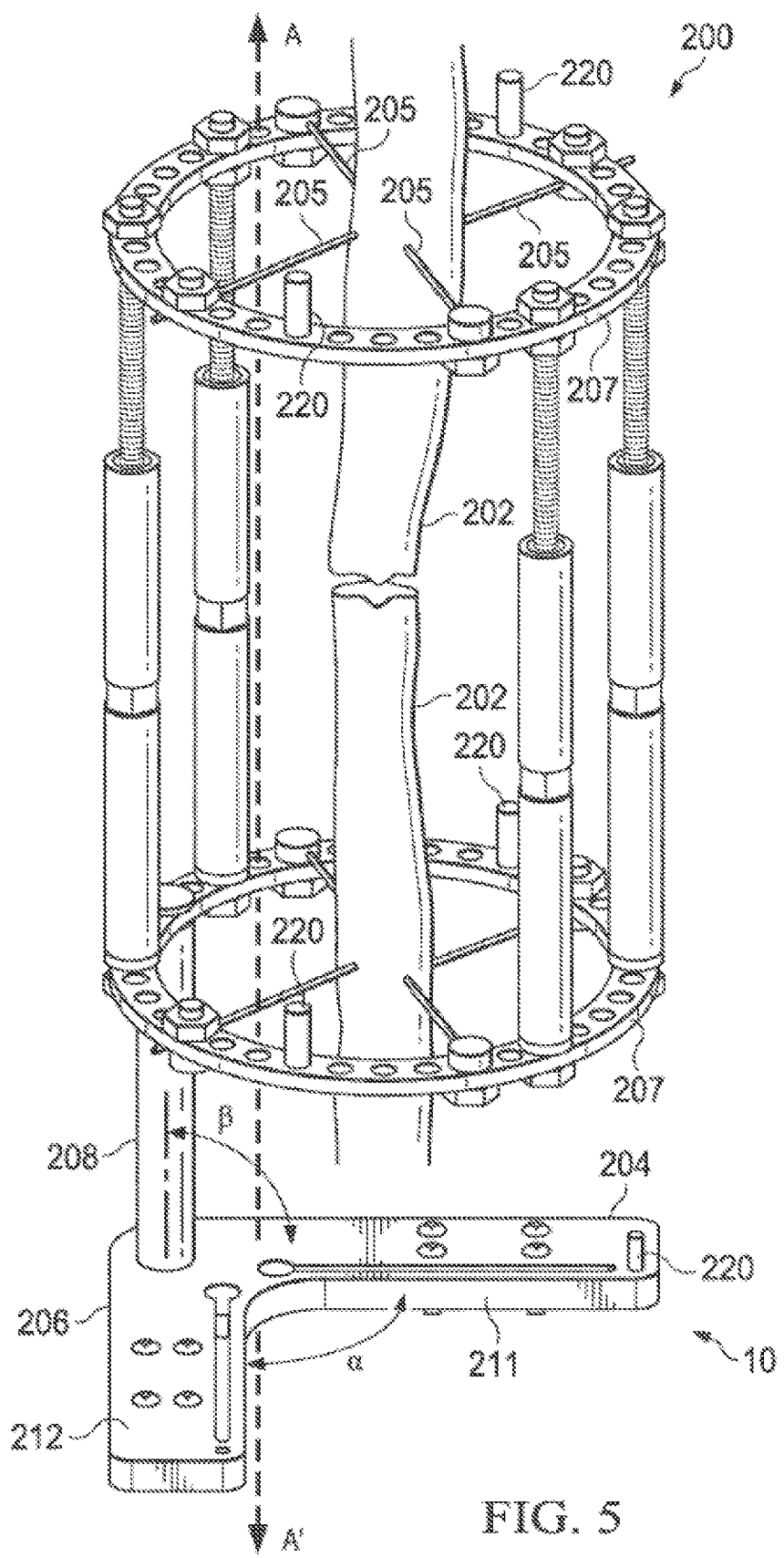
FIG. 5 shows a perspective view of the radiography aid according to FIGS. 1A-1C that is connected to an external fixator ring, which is also connected to a patient's anatomy.

A detailed view of a representative radiographic system 200 is depicted in FIG. 5, in which the various angles, surfaces and the radiographic body 10 are illustrated. Briefly, the radiographic body 10 is depicted with an object 202 (such as a fractured long-bone) affixed to the external fixation device 50 connected via pins 205, which rigidly hold the object 202 in place in relation to the external fixation device 50. The external fixation device 50 is depicted as comprising rings 207, however, a skilled artisan will recognize that the external fixation device 50 can have other shapes and even have open ends, or be temporarily or permanently attached to the object 202. This embodiment is shown connecting the external fixation device 50 with at least one strut 208 to the radiographic body 10. Additional struts 208 may be added to provide additional stability to the system 200, as shown in FIG. 3. A longitudinal axis A-A' of the radiographic system 200 system is shown, as are a first angle α formed between the arms 211, 212 of the radiographic body 10, and a second angle β that is formed between the plane formed by the radiographic body 10 and the longitudinal axis A-A' of the radiographic system 200, which can also be the angle formed between the strut 208 and the radiographic body 10, if the strut 208 is parallel to the longitudinal axis A-A' of the radiographic system 200. The radiographic body 10 include a first surface 204 and a second surface 206 located on outer surfaces of the arms 211, 212 from the first angle α. The first and second surfaces 204, 206 will be used in the operation of the radiographic system 200. Also shown in FIG. 5 is a set of radiographic markers 220, which are depicted as being attached to one or both of the rings 207 and to the arm 204. These markers, when used with the known dimensions of the rings and the device 10, can help determine the three-dimensional position of the imaged portion of the body on the radiograph, through known techniques.

Figure 6A:
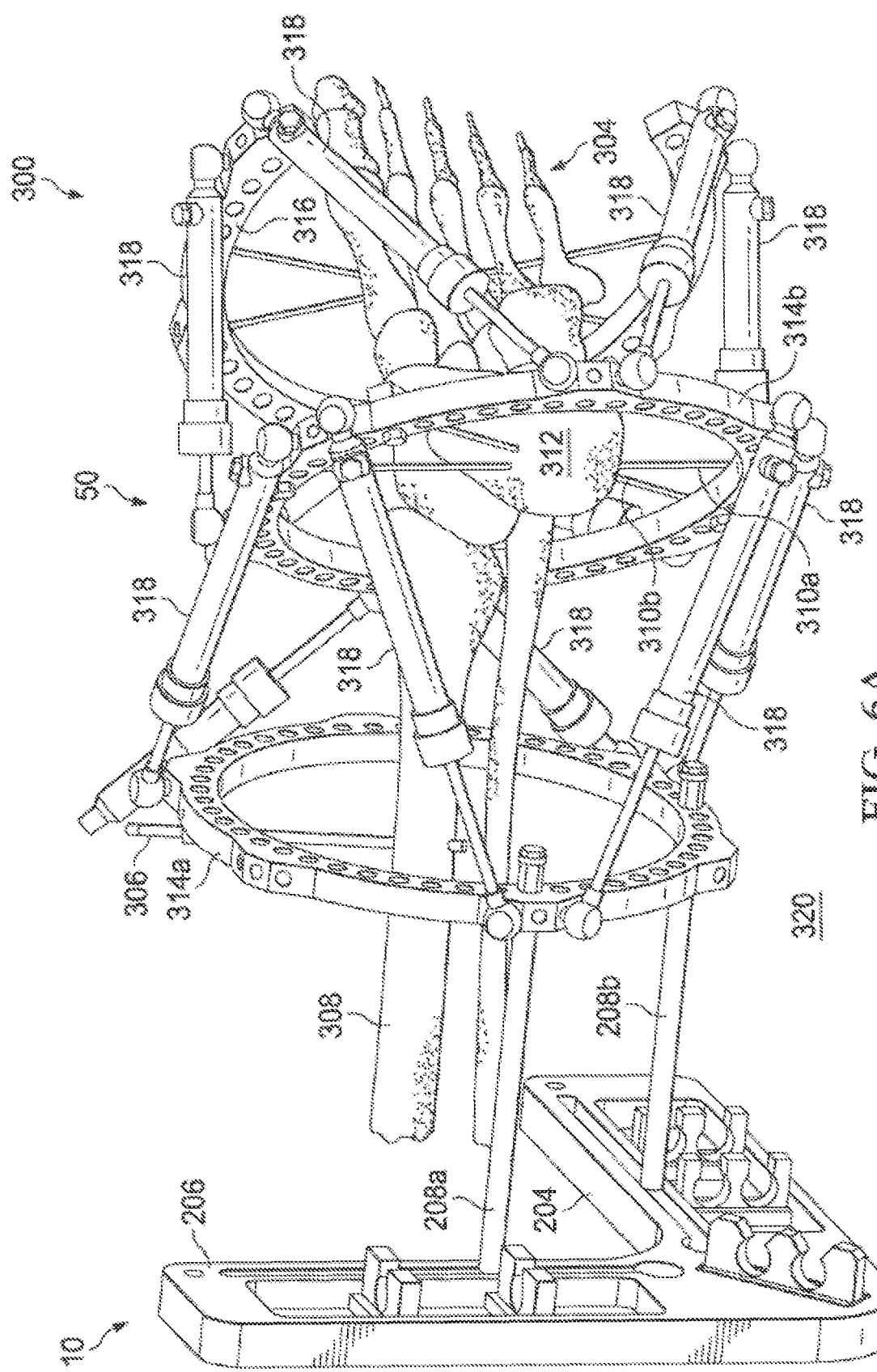
FIG. 6A shows a perspective view of the radiography aid according to FIGS. 1A-1C that is connected to an external fixator system, which is also connected to a patient's anatomy.

An exemplary use of the radiographic system 300 is depicted in FIG. 6A. The radiographic body 10 is shown connected via struts 208a, 208b to the external fixation device 50. The external fixation device 50 in this implementation is placed around the bones of the tibia 308 and foot 304 and connected via a heavy pin 306 to the tibia 308. Smaller pins 310a, 310b are shown traversing the calcaneus bone 312, depicted in this figure from a posterior view. The external fixation device 50 includes two full rings 314a, 314b, and also a partial ring 316, held together by a plurality of external fixation struts 318. FIG. 6A depicts the radiographic body 10 on a surface of table 320, which would generally be the surface of a radiographic machine along a first surface 204. The second surface 206 is at a 90 degree angle from the first surface, and the second surface 206 is not in contact with the table 320. The image of the tibia 308 and foot 304 obtained would be from a side or lateral view of the tibia 308 and foot 304 when a radiograph is taken from the side opposite the table 320.

Figure 6B:
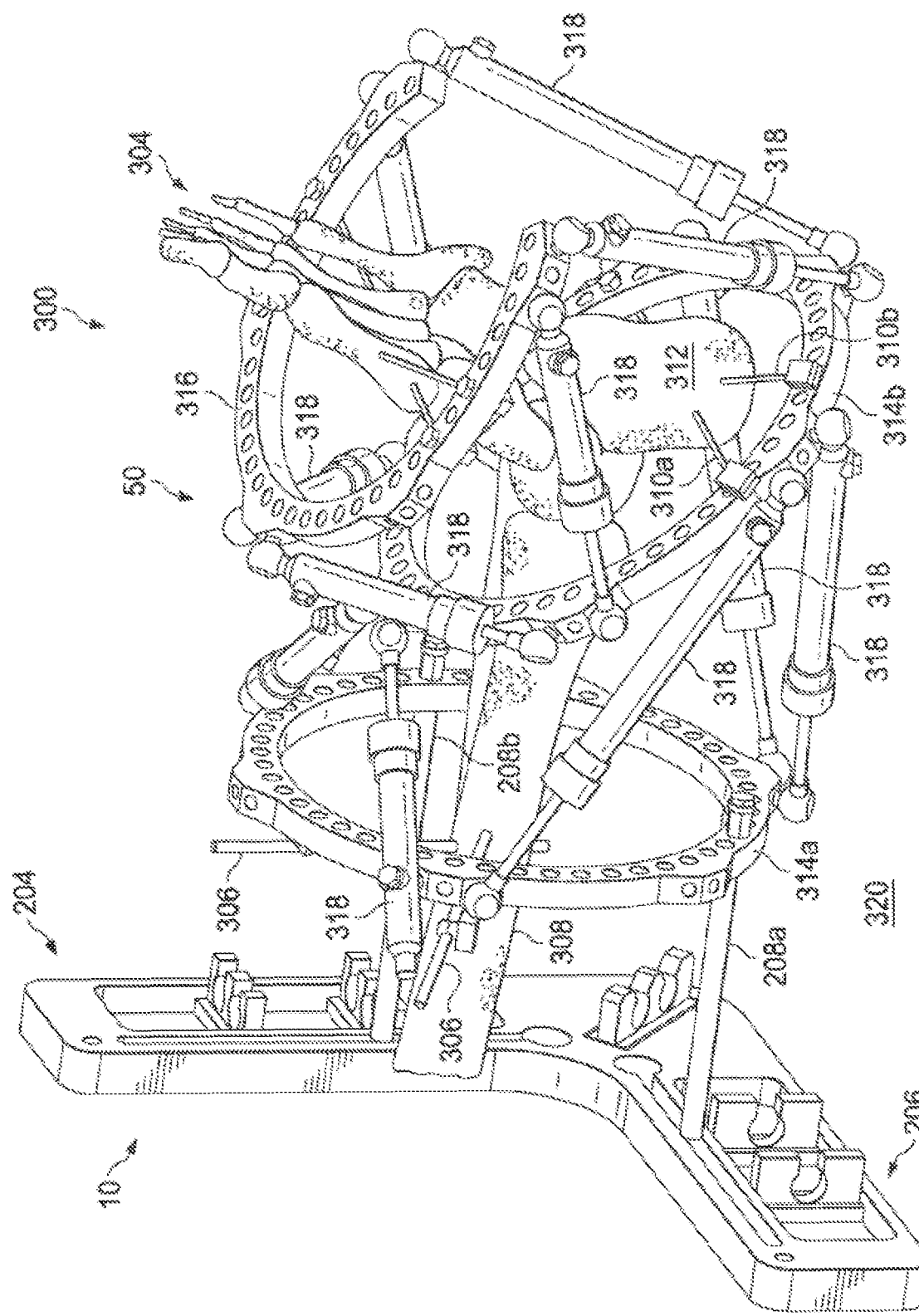
FIG. 6B shows an alternative perspective view of the radiography aid according to FIGS. 1A-1C that is connected to an external fixator system, which is also connected to a patient's anatomy.

Another view of an exemplary use of the radiographic system 300 is depicted in FIG. 6B. In FIG. 6B, the radiographic body 10 is shown connected via struts 208a, 208b to the external fixation device 50. The external fixation device 50 in this implementation around the bones of the tibia 308 and foot 304 are connected via a heavy pin 306 to the tibia 308. Smaller pins 310a, 310b are shown traversing the calcaneus bone 312, depicted in this figure from a lateral view. The external fixation device 50 includes two full rings 314a, 314b, and also a partial ring 316, held together by a plurality of external fixation struts 318. This figure depicts the radiographic body 10 on a surface 320, which would generally be the surface of a radiographic machine, along a second surface 206. The first surface 204 is not on the table 320. The image of the foot 304 and tibia 308 obtained by changing the position 90 degrees would by a front or anterior view of the tibia 308 and foot 304 when a radiograph is taken from the side opposite the table 320. Thus, the user would use the radiographic body 10 to obtain two images of the tibia 308 and foot 304 that are separated by the angle of the radiographic body 10, which in these figures is 90 degrees.

In this way, a rigid system for substantially perpendicular radiographs is connected to the external bone fixation device and the radiography aid designed in accordance with the present disclosure is obtained. In operation, the patient will rest or will be helped to rest his/her body or limb with the fractured bone(s), for example the tibia of the leg, on a radiological table so as to undergo a first radiograph. Next, using the edges of the radiographic body arranged with precision at right angles, the patient or limb is rotated 90° and assisted the radiography aid which, being provided by first and second surfaces 204 and 206, which are perpendicular to each other, and that enables a second radiograph which is substantially perpendicular to the first radiograph.

Figure 7:
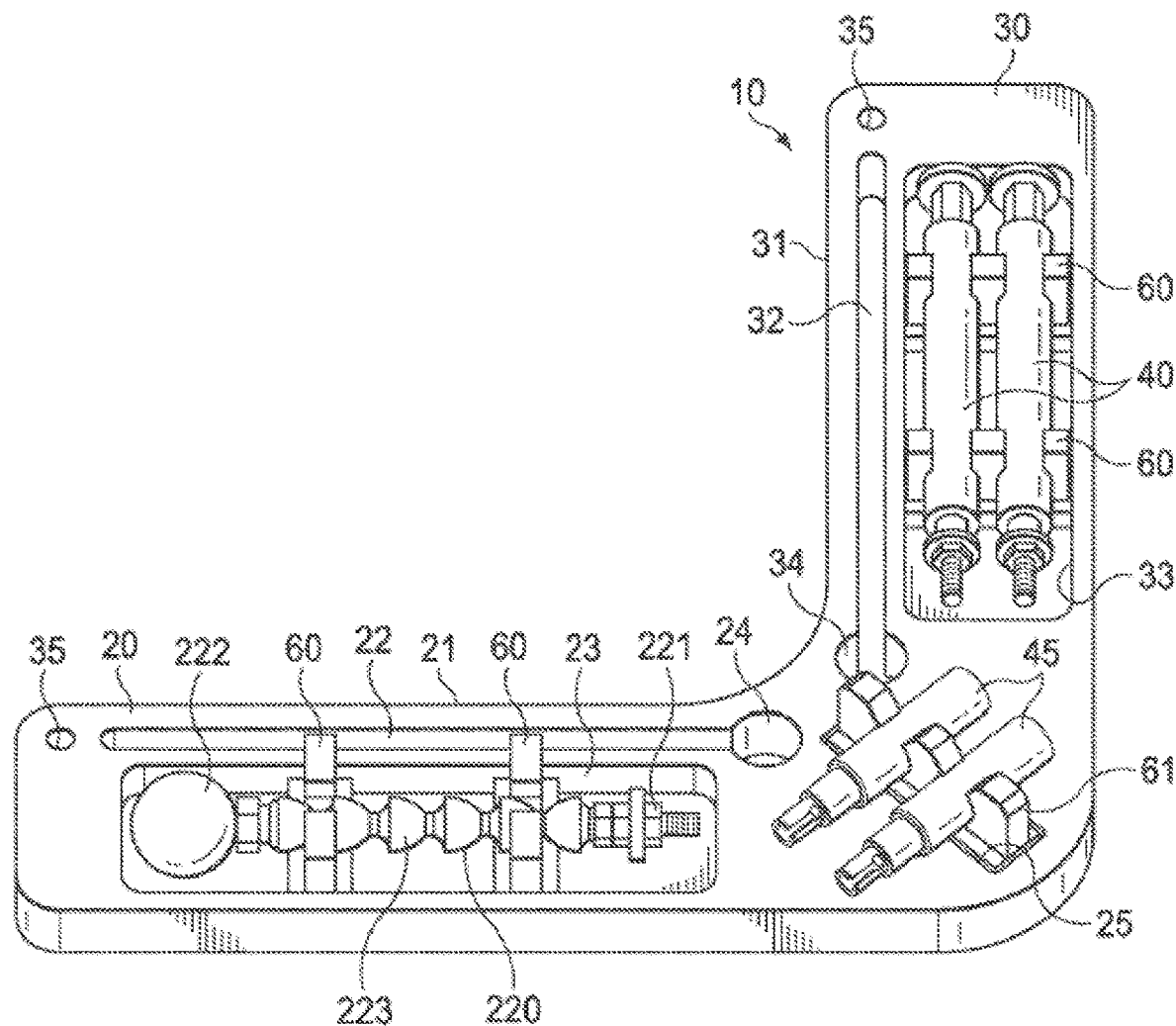
FIG. 7 shows a perspective view of the radiography aid according to FIGS. 1A-1C, along with the components that can be releasably attached to the body.

Another representative embodiment of a radiographic body 10 is depicted in FIG. 7. In FIG. 7, the radiographic body 10 comprises a first arm 20 having a first wall 21 and a second arm 30 having a second wall 31 arranged with precision at right angles to the first wall 21. Each of these arms 20, 30 of the radiographic body 10 may be furthermore provided with longitudinal slits 22, 32 parallel to the respective walls 21, 31 and terminating in apertures 24, 34 of sufficient size to permit the insertion and connection of fasteners, rods, or struts, which are able to ensure connection of the body 10 to an external fixator when the fixator is mounted and fixed onto a patient's bone. Each arm 20, 30 can be provided with a respective recess 23, 33 into which a pair of snap-engaging seats 60 made of resilient material can be included to provide storage for fixators, bolts, nuts, rods, shafts, markers, radiographic markers, or even one or more levels can be included. Also shown in FIG. 7 is an additional recess 25 with smaller dimensions in the corner portion between the arms 20, 30 to insert a further snap-engaging seat 61 or opening for a fastener, rod or shaft. These snap-engaging seats can be used to releasably connect fasteners, rods, struts, or other devices to attach the radiographic body 10 to the external bone fixation device 100. A representative embodiment of a radiographic marker 220 is depicted in FIG. 7. The depicted radiographic marker 220 is a magnification marker, which includes a threaded bolt and screw 221, which can be used to attach the marker 220 to the body 10 at apertures 35, or to an external fixator device, as shown in FIGS. 3, 4, and 5. The radiographic marker 220 includes a radiopaque component 222 of a known shape and size (depicted in FIG. 7 as a sphere) to calibrate the distances measured in the first and second radiographic images taken of the patient. Also depicted in FIG. 7 is a flexible arm 223, which allows the radiopaque component 222 to be positioned in a desirable location during the radiograph process. According to another embodiment, the radiographic marker 220 includes a rigid shaft of a known length that can also be attached to the body 10, or to an external fixator device. Further shown in FIG. 7 is a pair of fixation struts 40 mounted in the snap-engaging seats 60 of the recess 33. The fixation struts 40 can be fixed via one of its ends to the radiographic body 10 by passing through the apertures 24, 34 and sliding into an appropriate location in the slots 22, 32, and via the other opposite end fixed to an external fixation ring 50. The lengths of the longitudinal slits 22, 32 with apertures 24, 34 at their ends is such as to allow insertion of the end of the rod with the bolt already mounted through the apertures 24, 34 and sliding and positioning of the rod 40 at the most suitable point, followed by tightening of the bolt depending on the diameter of the ring of the external bone fixation device. Once the external fixation ring 50 is fixed to the radiographic body 10 via rods or struts 40, the external fixation ring 50 and the radiographic body 10 are rigidly fixed together. Therefore, rotation of the external fixation ring 50 also causes rotation of the radiographic body 10 and vice versa. Also shown in FIG. 7 are a pair of ring centering pins 45, which can be used to indicate the center of fixator rings that are attached to the body 10 in a radiograph. Each centering pin 45 includes a radiopaque marker (not shown) embedded within an end of the pin opposite to where it is attached to a fixator ring. The centering pins 45 can be attached to a predetermined location on the fixator rings 207 in the same way as markers 220, as shown in FIG. 5. Preferably, the centering pins 45 are attached to the "zero" holes of an external fixator ring (one anterior and one posterior), thus allowing a radiologist or technician to measure the center of the rings in a radiograph. The centering pins 45 can therefore help calculate frame mounting parameters necessary for software, specifically anterior, posterior, medial, lateral offsets (distance in mm from the axis of the bone to the center of the ring) for therapeutic treatment of the patient.

An alternative embodiment of a centering pin 45 is depicted in FIG. 8. In FIG. 8, the centering pin 45 is comprised of a radiopaque material and includes a threaded portion and nut 46, which can be used to attach the centering pin 45 to an external fixator device, as shown in FIGS. 3, 4, and 5. The centering pin 45 may also include a marker 47 of a known shape and size (depicted in FIG. 8 as a 10 mm sphere) to calibrate the distances measured in the first and second radiographic images taken of the patient and ensure proper alignment of the external fixator rings. The marker 47 is attached to the shaft 48 of a predetermined length of a centering pin 45.

Figure 9A:
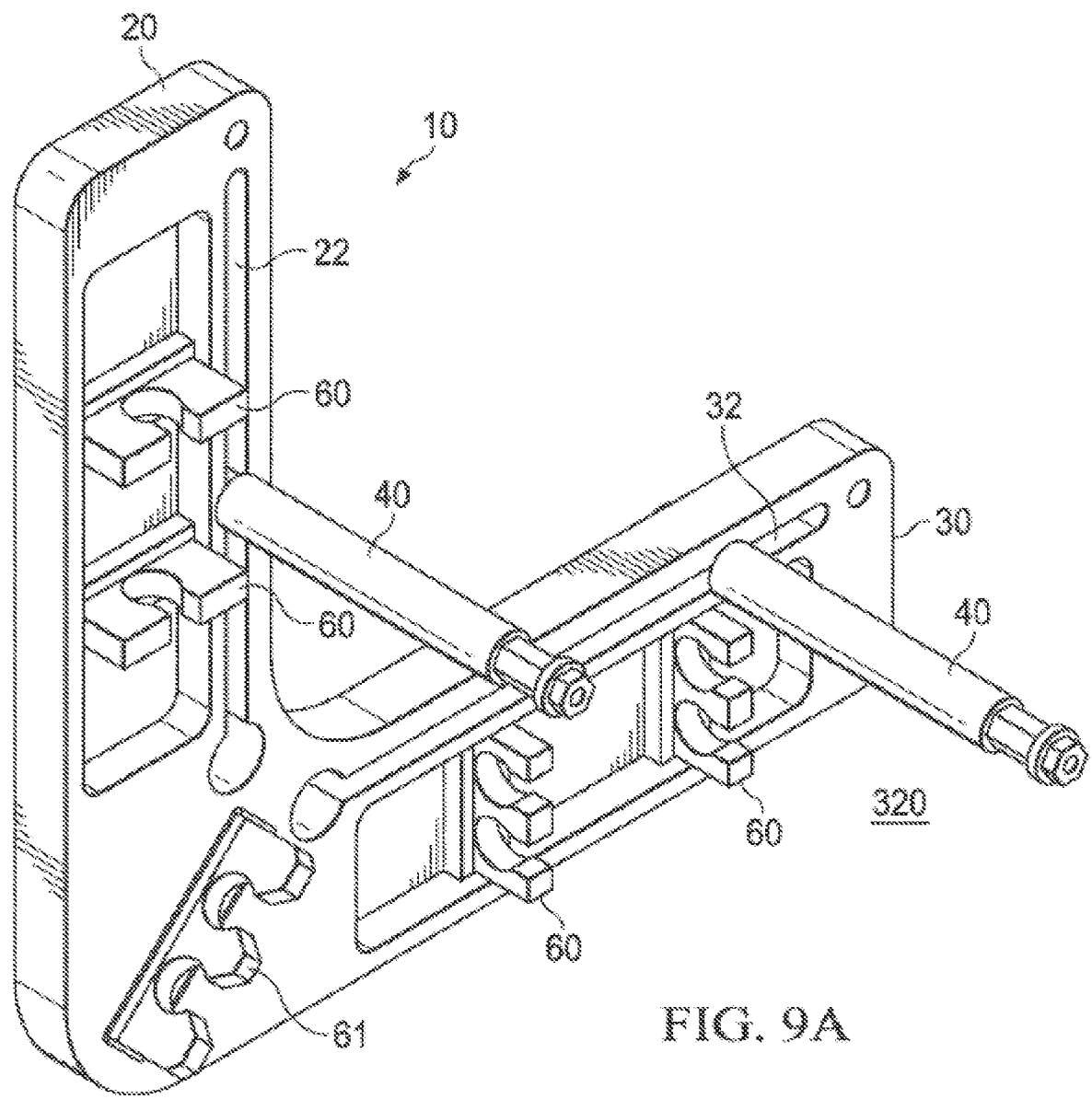
FIG. 9A shows a perspective view of the radiography aid according to FIGS. 1A-1C with a pair of struts mounted to the device.
Figure 9B:
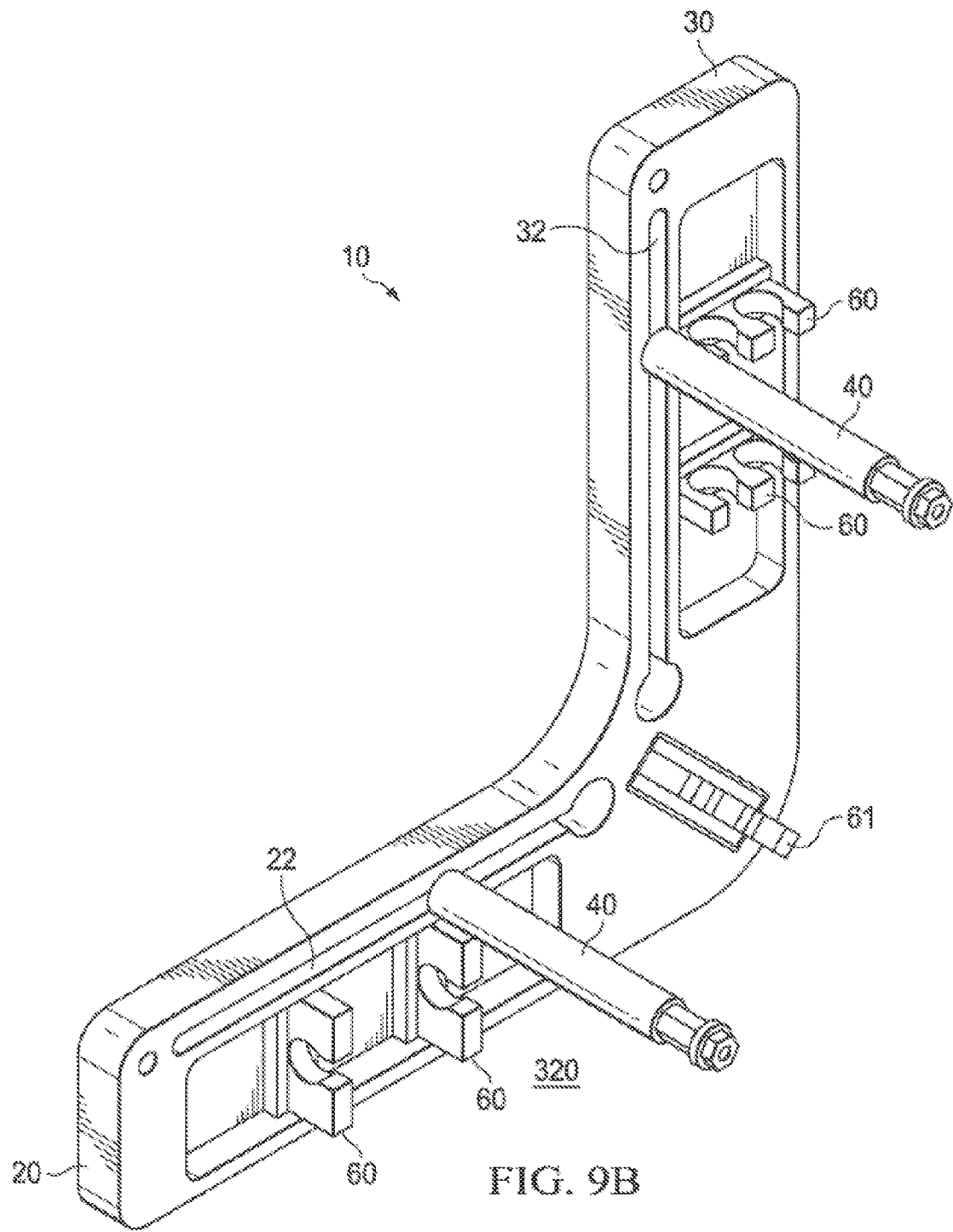
FIG. 9B shows another perspective view of the radiography aid according to FIGS. 1A-1C with a pair of struts mounted to the device.

Additional representative embodiments of the radiographic body 10 are depicted in FIGS. 9A and 9B. In these figures, struts 40 have been attached to the body 10 in the slots 22 and 32 of arms 20 and 30, respectively. These struts 40 can be connected to an external fixation device 200 that has a longitudinal axis A-A' that is generally parallel with the outer surfaces (204, 206) of the body 10, similar to the embodiment depicted FIG. 5. For purposes of simplicity, the external fixation device 200 is not shown in FIGS. 9A and 9B. The components that are usually stored in the snap-engaging seats 60, 61 have been removed so that they do not impair or interfere with the radioimaging process. FIG. 9A demonstrates how the second arm 30 of the radiographic body 10 will rest upon an imager surface 320 during a first radiograph. The second arm 30 has an outer surface with a width of about 10-50 mm that lies in contact with the imager surface 320. Preferably, the outer surface has sufficient width to provide a stable platform for holding the external fixator in a fixed position with respect to the imager during the first radiograph. FIG. 9B demonstrates how the first arm 20 of the radiographic body 10 will rest upon an imager surface 320 during a second radiograph. The first arm 20 has an outer surface with a width of about 10-50 mm that lies in contact with the imager surface 320. Preferably, the outer surface has a sufficient width to provide a stable platform for holding the external fixator in a fixed position with respect to the imager during the second radiograph.

It is contemplated that any embodiment discussed in this specification can be implemented with respect to any method, kit, reagent, or composition, and vice versa. Furthermore, a variety of compositions can be used to achieve methods disclosed herein.

It will be understood that particular embodiments described herein are shown by way of illustration and not as limitations of the invention. The principal features described in this disclosure can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), propertie(s), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

What is claimed is:

1. A method of determining a position of one or more bones affixed to an external fixation device in three dimensions comprising:
    attaching a radiographic reference device to the external fixation device, wherein the radiographic reference device comprises a first arm having a first surface and a second arm having a second surface, the first and second surfaces separated by a first angle, wherein the at least two surfaces of the radiographic reference device are positioned at a second angle relative to a longitudinal axis of the external fixation device, wherein the one or more bones extend through an opening formed in the radiographic reference device between the first arm and the second arm;
    positioning the first surface of the radiographic reference device on a surface to capture a first radiographic image of the external fixation device and the one or more bones;
    repositioning the external fixation device to position the second surface of the radiographic reference device on the surface to capture a second radiographic image of the external fixation device and the one or more bones that differs in position from the first radiographic image by the first angle; and
    calculating the position of the one or more bones in three dimensions based on distances measured from the first and second radiographic images with the first and second angles.

2. The method of claim 1, wherein the radiographic reference device is attached to the external fixation device with one or more rods or struts.

3. The method of claim 1, wherein the first and second angles are selected from the group consisting of 30°, 45°, 60°, 75°, 90°, 105°, 120°, and 150° degrees.

4. The method of claim 1, further comprising positioning a size marker attached to at least one of the external fixation device, a strut, or the radiographic reference device, wherein the size marker provides a known size to calibrate the distances measured in the first and second radiographic images.

5. The method of claim 2, wherein the one or more struts are adjustable-length struts.

6. The method of claim 1, wherein the radiographic reference device is at least partially radiotranslucent.

7. The method of claim 1, wherein the radiographic reference device is plastic, polymer, metal, ceramic, wood, or a composite.

8. The method of claim 2, wherein the radiographic reference device further comprises a slot adapted to receive the one or more struts.

9. The method of claim 1, wherein the radiographic reference device is substantially flat.

10. The method of claim 2, wherein the radiographic reference device further comprises one or more storage compartments for storing one or more radiographic markers and the one or more struts.

11. The method of claim 1, wherein the one or more bones comprise a tibia.

12. The method of claim 1, wherein the first arm comprises a first slot that extends longitudinally along a length of the first arm and the second arm comprises a second slot that extends longitudinally along a length of the second arm, the first slot being substantially perpendicular to the second slot, and wherein attaching the radiographic reference device to the external fixation device includes both securing a first rod or strut between the first slot and the external fixation device and securing a second rod or strut between the second slot and the external fixation device.

13. The method of claim 1, wherein the first and second arms have substantially the same length.

14. The method of claim 1, further comprising attaching a radiographic marker to the radiographic reference device.

15. A system for determining a position of one or more objects affixed to an external fixation device in three dimensions comprising:
 a radiographic reference device attachable to the external fixation device, wherein the radiographic reference device comprises at least two surfaces separated by a first angle, wherein the at least two surfaces of the radiographic reference device are positioned at a second angle relative to a longitudinal axis of the external fixation device;
 a size marker having a known size, wherein a first radiographic image and a second radiographic image are each taken with a radiography device while the size marker is secured to the radiographic reference device or the external fixation device, wherein the first radiographic image is acquired when the first surface of the radiographic reference device is on a surface, and the second radiographic image is taken when the second surface of the radiographic reference device is on the surface; and
 a processor that calculates the position of the one or more objects in three dimensions based on distances measured from the first and second radiographic images with the first and second angles, the distances being calibrated by the known size of the size marker appearing in the first and second radiographic images.

16. The system of claim 15, further comprising one or more struts, wherein the radiographic reference device is attached to the external fixation device with one or more rods or the one or more struts.

17. The system of claim 15, wherein the first and second angles are selected from the group consisting of 30°, 45°, 60°, 75°, 90°, 105°, 120°, and 150° degrees.

18. The system of claim 16, wherein the one or more struts are adjustable struts.

19. The system of claim 15, wherein the radiographic reference device is at least partially radiotranslucent.

20. The system of claim 15, wherein the radiographic reference device is plastic, polymer, metal, ceramic, wood, or a composite.

21. The system of claim 16, wherein the radiographic reference device is defined further as comprising a slot adapted to receive the one or more struts.

22. The system of claim 15, wherein the radiographic reference device is substantially flat.

23. The system of claim 16, wherein the radiographic reference device further comprises one or more storage compartments for storing one or more radiographic markers and the one or more struts.

24. The system of claim 15, wherein the one or more objects comprise at least one bone.

25. The system of claim 15, first and second surfaces of the radiographic reference device are defined further as comprising a first and second arm, respectively.

26. The system of claim 25, wherein each of the first and second arms comprise longitudinal slits extend longitudinally along the respective arm and are substantially perpendicular to each other.

27. The system of claim 25, wherein the radiographic reference device has a right-angled shape with the first and second arms having substantially the same length.

28. The system of claim 15, further comprising a radiographic marker adapted to be attached to at least one of the radiographic reference device or the external fixation device.

29. A system for determining a position of one or more objects affixed to an external fixation device in three dimensions comprising:
 a radiographic reference device attachable to a ring of the external fixation device disposed around the one or more objects, wherein the radiographic reference device comprises at least two surfaces separated by a first angle, wherein the at least two surfaces of the radiographic reference device are positioned at a second angle relative to a longitudinal axis of the external fixation device, wherein the radiographic reference device is configured for obtaining a first radiographic image and a second radiographic image taken with a radiography device, wherein the first radiographic image is acquired when the first surface of the radiographic reference device is on a surface, and the second radiographic image is taken when the second surface of the radiographic reference device is on the surface;
 a radiographic marker including a radiopaque component having a known size and a flexible arm for positioning the radiopaque component; and
 a processor configured to calculate the position of the one or more objects in three dimensions based on distances measured from the first and second radiographic images with the first and second angles, the distances being calibrated using the known size of the radiopaque component.

30. A kit comprising:
 a radiographic reference device comprising:
  a first arm having a first surface;
  a second arm having a second surface perpendicular to the first surface; and
  a plurality of resilient snap-engaging seats; and
 a plurality of rods or struts configured to attach the radiographic reference device to a ring of an external fixation device, wherein the plurality of resilient snap-engaging seats are configured to retain the plurality of rods or struts on the radiographic reference device.

31. The kit of claim 30, further comprising at least one of a leveling instrument or a ring centering pin including a radiopaque marker, wherein the plurality of resilient snap-engaging seats are further configured to retain the at least one of the leveling instrument or the ring centering pin on the radiographic reference device.

32. The method of claim 1, wherein attaching the radiographic reference device to the external fixation device comprises attaching a first fastener to a first aperture extending into a surface of the first arm opposite the first surface and attaching a second fastener to a second aperture extending into a fourth surface of the second arm opposite the second surface.

* * * * *